(12) United States Patent
Danielzik et al.

(10) Patent No.: US 6,211,954 B1
(45) Date of Patent: Apr. 3, 2001

(54) INTEGRATED OPTICAL LUMINESCENCE SENSOR

(75) Inventors: Burkhard Danielzik, Ingelheim (DE); Dieter Neuschäfer, Muttenz (CH); Michael Pawlak, Laufenburg; Gert Ludwig Duveneck, Bad Krozingen, both of (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/155,617
(22) PCT Filed: Mar. 22, 1997
(86) PCT No.: PCT/EP97/01468
§ 371 Date: Nov. 5, 1999
§ 102(e) Date: Nov. 5, 1999
(87) PCT Pub. No.: WO97/37211
PCT Pub. Date: Oct. 9, 1997

(30) Foreign Application Priority Data

Mar. 30, 1996 (DE) .............................. 196 12 868

(51) Int. Cl.[7] .................................................. G01N 21/64
(52) U.S. Cl. ........................ 356/317; 385/12; 250/458.1
(58) Field of Search ..................... 356/311, 317, 356/318, 417; 250/458.1, 459.1, 461.1, 461.2; 385/12

(56) References Cited

U.S. PATENT DOCUMENTS 5,081,012    1/1992    Flanagan et al. ................ 435/7.9

FOREIGN PATENT DOCUMENTS

| 4433753 | 5/1995 | (DE) . |
|---|---|---|
| 8909394 | 10/1989 | (WO) . |
| 9301487 | 1/1993 | (WO) . |
| 9533197 | 12/1995 | (WO) . |
| 9533198 | 12/1995 | (WO) . |

OTHER PUBLICATIONS

Christensen et al., "Analysis of Excitation and Collection Geometries for Planar Waveguide Immunosensors", SPIE, vol. 1886 Fiber Optic Sensors in Medical Diagnostics, 1993, pp. 2–8.

Primary Examiner—F. L. Evans
(74) Attorney, Agent, or Firm—Wenderoth, Lind & Ponack, LLP.

(57) ABSTRACT

An integrated-optical luminescence sensor having an excitation light beam with a first optical axis ($k_{ein}$), a planar waveguide (1), a sample interacting with the evanescent field thereof, and a detection beam path, with a second optical axis, that comes from the waveguide, and/or a coupling-out grating (7) for coupling out the portion of luminescence light guided in the waveguide, wherein the luminescence light to be detected is physically separate from the excitation light.

17 Claims, 5 Drawing Sheets

FIG. 2
State of the Art

FIG. 3
State of the Art

INTEGRATED OPTICAL LUMINESCENCE SENSOR

BACKGROUND OF THE INVENTION

The invention relates to an integrated-optical luminescence sensor having an excitation light beam with a first optical axis, a planar waveguide, a sample interacting with the evanescent field thereof, and a detection beam path, with a second optical axis, that comes from the waveguide, or a luminescence detector, which represents a variant in the definition of the invention.

The invention relates especially to an integrated-optical luminescence sensor having an excitation light beam with a first optical axis, a planar waveguide, a sample interacting with the evanescent field thereof, and a detection beam path, with a second optical axis, that comes from the waveguide, and/or a coupling-out grating for coupling out the portion of the luminescence light guided in the waveguide, wherein the luminescence light to be detected by means of a luminescence detector is physically separate from the excitation light.

According to the state of the art, such sensors are employed to operate surface-sensitive optical substance sensors. In affinity sensory analysis, the molecules to be detected are selectively bound to the sensor surface and are detected by interaction with the guided lightwave. In the case of direct affinity sensory analysis, this is effected by measuring changes in refractive index, or another possible method is to detect the luminescence radiation excited by the guided wave.

The use of planar waveguides for the detection of luminescent substances is described in D. Christensen et al. Proc. SPIE 1886 (1993), 2–8. The beam path lies in one plane, so that in order to suppress reflections and scattered light (for example from the edges of the sensor) it is necessary to use dichroic beam splitters and cut-off filters, giving rise to adverse effects on the dynamic range and the detection sensitivity.

Sensors having planar waveguides and one or more grating couplers for coupling in and/or coupling out the guided waves are known, for example, from WO 93/01487, but only for the direct method of detection by means of the change in refractive index.

A disadvantage that may arise in the use of those arrangements for luminescence detection is that the beam is generally guided in an optical plane perpendicular to the waveguide surface (that is to say k-vectors of coupled-in and coupled-out radiation lie in one optical plane) and hence, in order to separate the excitation light and luminescence light and to suppress reflections and scattered light, those arrangements, likewise, require provisions such as dichroic beam splitters, screens, interference filters, notch filters or cut-off filters.

In the arrangement described in U.S. Pat. No. 5,081,012, which uses coupling gratings, the excitation light and luminescence light are coupled collinearly, or the excitation beam path and luminescence beam path lie in one optical plane. For the physical separation of those light components it is necessary to use curved grating lines, with the result that the production of the sensor element is very complex.

A method and an arrangement of that kind are also described in WO 95/33198, which is to be considered as part of this disclosure.

The problem underlying the invention is to render possible low-background-noise, high-sensitivity luminescence detection using an optical sensor platform having a coupling grating in which physical separation of excitation light, including reflections and luminescence light is achieved by the manner in which the excitation light and luminescence light beams are guided or by the utilization of different polarization properties of excitation light and luminescence light.

SUMMARY OF THE INVENTION

The problem is solved in a first embodiment of the present invention by using a luminescence sensor, the luminescence light incident on a suitable detector is physically separate from the excitation light by virtue of the geometric arrangement of the optical axes ($k_{ein}$, 61) and/or by the use of polarization-selective optical components in the outgoing detection beam path (60)

and/or by polarization-selective detection of the portion of luminescence radiation coupled out by a coupling-out grating (7)

and/or by polarization-selective detection of the by a grating (4) acting as coupling-out grating for the excitation radiation, which grating is also used to couple in the excitation light.

That physical separation of the luminescence light incident on the detector from the excitation light may especially be achieved by an arrangement in which the two optical axes ($k_{ein}$, 61) are skew relative to one another according to a second embodiment.

In known sensors those axes have always been coplanar in highly symmetrical arrangements, as is customary and expedient in "direct" sensors which evaluate changes in refractive index.

The solution in a second embodiment removes the symmetry of the sensor at the earliest possible stage, and according to the second part of a fourth embodiment tilts the entry plane relative to the coupling-in plane. The angle of tilt is approximately from 1° to 30°, preferably from 2° to 15°, and is oriented to the angle of divergence of the excitation light beam, as well as to that of the detection beam path. The corresponding arrangement relate to advantageous further developments.

A third embodiment describes the variant in which the luminescence radiation emitted into space is captured without being influenced by the waveguide, while a fourth embodiment provides for the capture of the luminescence light coupled into the waveguide using a coupling-out grating. Also possible and expedient is the simultaneous execution of both kinds of detection.

This configuration is especially insensitive to minor misalignments and variations in angle, which is of great importance especially when the sensor is changed and for accommodating manufacturing tolerances in the sensor.

A further advantage of the arrangement according to the invention is that it is possible for the beam guidance system to be compactly constructed in an integrated module in which all light beams necessary for the use of the sensor can be coupled in, coupled out and detected. The miniaturization facilitated is also advantageous in reducing interfering influences caused by the environment, such as, for example, external light and vibration.

A fifth embodiment also relates to the capture of the luminescence light coupled into the waveguide, but the coupling-in grating provided for coupling in the excitation light is used. This arrangement is possible since the luminescence light coupled into and guided in the waveguide surprisingly has no preferred direction of propagation. Again, simultaneous execution of this method of detection together with one or both of the previously described methods of detection is also possible. In addition, that arrangement has the advantage that the same grating can be used both for coupling in the excitation light and for coupling out the luminescence light guided in the waveguide with subsequent detection.

A sixth embodiment relates to a specific arrangement of the skew geometry with the aim of obtaining as little interference as possible to the luminescence light by excitation light in the detector. Another possibility is a form (of arrangement) according to which the excitation light beam and the detection beam path are so configured in cross-section, divergence, orientation and point of meeting with the waveguide that it is not possible for light from the excitation light beam to pass into the detection beam path as a result of a single reflection off any face.

According to a seventh embodiment it is possible, in principle, to take advantage of the different polarization properties of excitation light and luminescence light if completely polarized excitation light, that is to say completely transversely magnetically polarized excitation light (TM), is used for the excitation of a TM mode guided in the waveguide, or completely transversely electrically polarized excitation light (TE) is used for the excitation of a TE mode guided in the waveguide. According to claim 8, in that arrangement it is advantageous for the detection of the luminescence light to select a polarization that is different from the polarization of the excitation light.

Of particular advantage is the polarization-selective detection of the portion of luminescence light coupled into the waveguide and coupled out with a coupling grating, since differently polarized light is coupled out at different angles. Consequently, the physical separation of coupled-out excitation light and coupled-out luminescence light, which is a consequence of the spectral shift and results in coupling out at different angles, can be significantly increased. Since the propagation of coupled-in luminescence light in the waveguide surprisingly occurs without a preferred direction, it is possible for coupled-in luminescence light to be coupled out either at a coupling-out grating (7) or at the grating (4) used for coupling in the excitation light, and be detected by a detector. When TE-polarized excitation light is used, it is preferred to detect the portion of TM-polarized luminescence light coupled into the waveguide that is coupled out by a coupling grating and, when TM-polarized excitation light is used, it is preferred to detect the portion of TE-polarized luminescence light coupled into the waveguide that is coupled out by a coupling grating.

If the portion of the luminescence, coupled into the waveguide, of a dipole radiating in the direct vicinity of the waveguide is calculated by means of the so-called Flelmholtz arrangement, which is described, for example, in Novotny, Journal of Optical Society of America A14, p. 91 (1997), then it is found, surprisingly, that the interaction with the evanescent field of the waveguide gives rise to a decrease in the luminescence life of the dipole and to the radiation of up to three times more photons per unit of time. The end result of those calculations is that those additional photons are coupled into the waveguide. The portion of the luminescence coupled into the waveguide can accordingly be up to three times as large as the light intensity radiated into the entire solid angle by the undisturbed dipole.

Embodiment Example 1 supports that finding.

Further preferred embodiments of the integrated-optical luminescence sensor according to the invention are those that consist of a single wave-guiding region in conjunction with a coupling-in grating (4) or a coupling-out grating (7) or both gratings. Also preferred are sensor platforms according to the invention that consist of several separate wave-guiding regions.

In the arrangements according to the invention, the luminescence radiation is physically separate from the excitation light at the detector.

The arrangements according to the invention are illustrated with reference to the drawings, which are intended merely to illustrate examples of embodiments. The drawings are not to be regarded as limiting the invention. For example, the various possible methods of polarization-selective luminescence detection explained hereinabove and the application of the arrangements of the integrated-optical luminescence sensor according to the invention to sensor platforms having several separate wave-guiding regions are not shown in the drawings but nevertheless, also in conjunction with the embodiments shown in the drawings, form part of the present invention.

BRIEF DESCRIPTION OF THE DRAWINGS

FIG. 4b is a section in an y-z plane of the arrangement according to FIGS. 1 and 4a;

FIG. 9b is a section in the y-z plane of FIG. 9a.

DETAILED DESCRIPTION OF THE INVENTION

Figure 1:
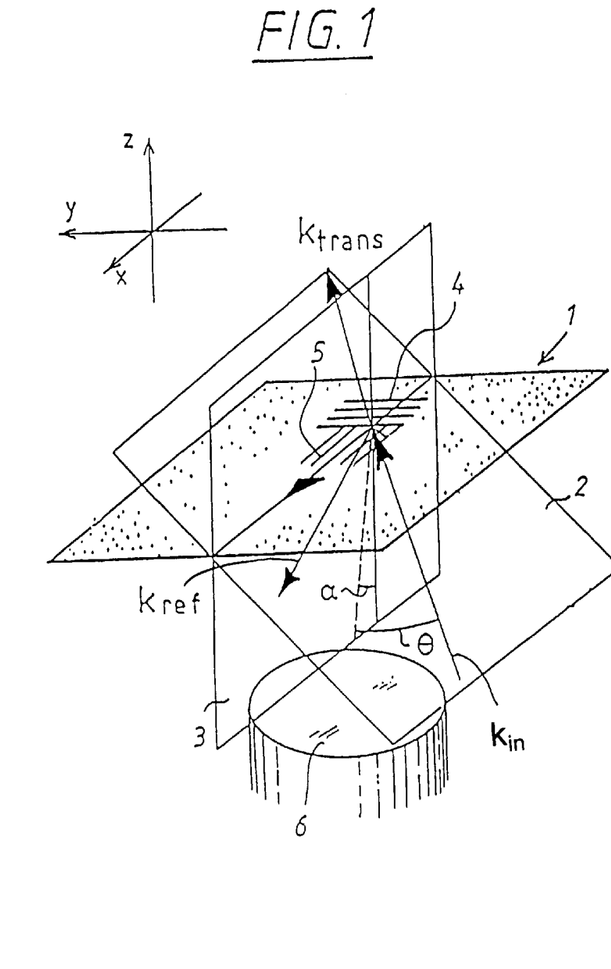
FIG. 1 is a diagrammatic representation of an arrangement according to the invention with detection of volume luminescence.
Figure 6:
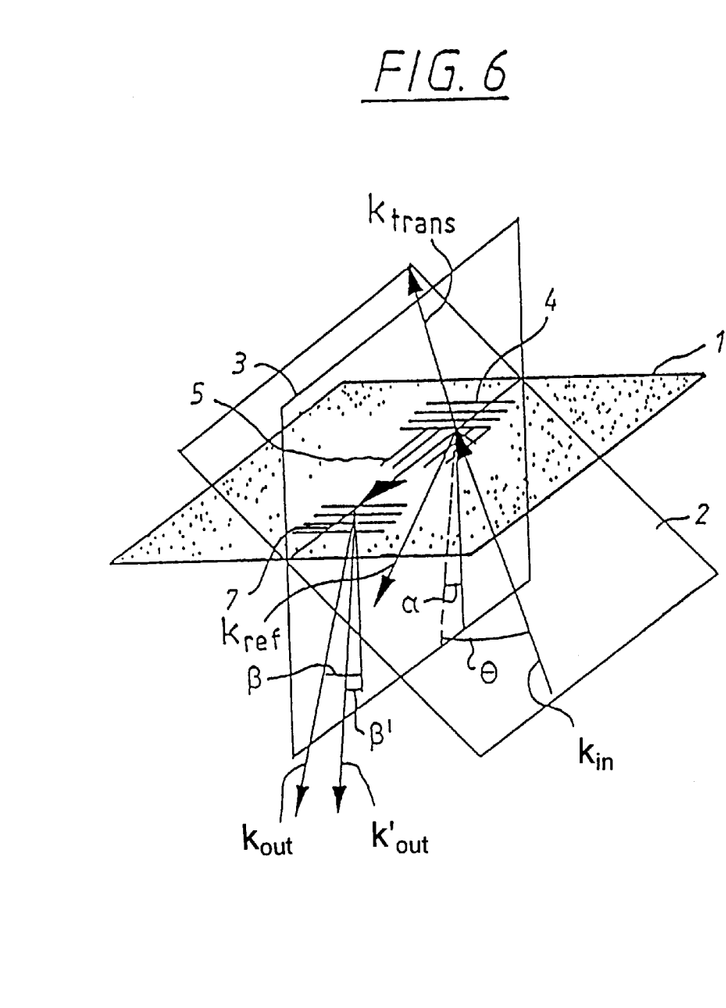
FIG. 6 is a diagrammatic representation of an arrangement according to the invention with detection of the luminescence coupled into the waveguide.

The Examples of FIGS. 1 and 6 give consideration to different methods of detecting luminescence radiation.

FIG. 1 shows the detection of volume luminescence. A portion of the luminescence radiation excited by the guided wave is emitted into the entire space; this portion can be captured by a focusing lens system (according to the solid angle captured by the lens system).

FIG. 6 shows the detection of the luminescence coupled into a waveguide. In addition to the luminescence radiation emitted into space, a portion is coupled into the waveguide again as a guided wave, and transported therein. There may be used for the detection in this arrangement, a coupling-out grating that is physically separate from the coupling-in grating and that may have an identical or different grating period. The coupling-out grating may in a further preferred geometry also be identical to the coupling-in grating. In both FIGS. 1 and 6 the liquid cell for supplying the sample is not shown.

For the specific (desired) use, it is necessary to choose from the two methods and arrangements taking into account: bond length and spacing of the molecules immobilized on the waveguide surface, effective mode refraction values of the radiation guided in the waveguide (dependent on refractive index and layer thickness), waveguide attenuation at excitation wavelength and luminescence wavelength, sensor area and sensor geometry, sample volume above the sensor and flow ratios in the sample cell. A combination of the two methods can also be used.

In the case of detection of volume fluorescence according to FIG. 1, a guided wave (5) having the wavelength of the incident light beam is excited by a coupling-in grating (4) in a plane of the waveguide (1) of the sensor. The luminescence of the sample in the region bordering the waveguide (1), excited by the evanescent field of the guided wave (5) and radiated into the entire solid angle, is for the most part captured by a focusing lens system (6) below the plane of the waveguide (1) of the sensor. A plane of incidence (2) is defined by the k-vectors of the incident (entry plane) light beam ($k_{ein}$) and the guided wave (5), and a coupling-in plane (3) is defined by the normal to the waveguide (1) and by the guided wave (5).

An angle θ is the angle between the plane of incidence (2) and the coupling-in plane (3). Because the excitation light radiated in lies outside the coupling-in plane (3), the k-vectors of the incident radiation ($k_{ein}$) lie in the plane of incidence (2), which is different from the coupling-in plane (3). Furthermore, by the use of backward coupling, that is to say the x-components of the k-vectors of the incident light beams ($k_{ein}$) and of the guided wave in the waveguide (1) having different directions, a further physical separation can be achieved by virtue of the different direction of propagation. As a result it is possible by making simple provisions to ensure that no direct ray portions of the excitation light can pass into the luminescence detector, for example by blackening and dulling the sample cell and mechanical units close to the sensor, and by using light traps for the transmitted and reflected portions ($k_{trans}$, $k_{ref}$) of the incident light rays. These provisions are fully effective even in the event of slight deviations of the coupling-in geometry from the reference values.

To illustrate the advantages of the coupling-in plane and the plane of incidence being different, the problems that arise in the volume fluorescence detection method in the absence of that provision, that is to say according to the state of the art, are discussed in detail in the as follows.

Figure 2:
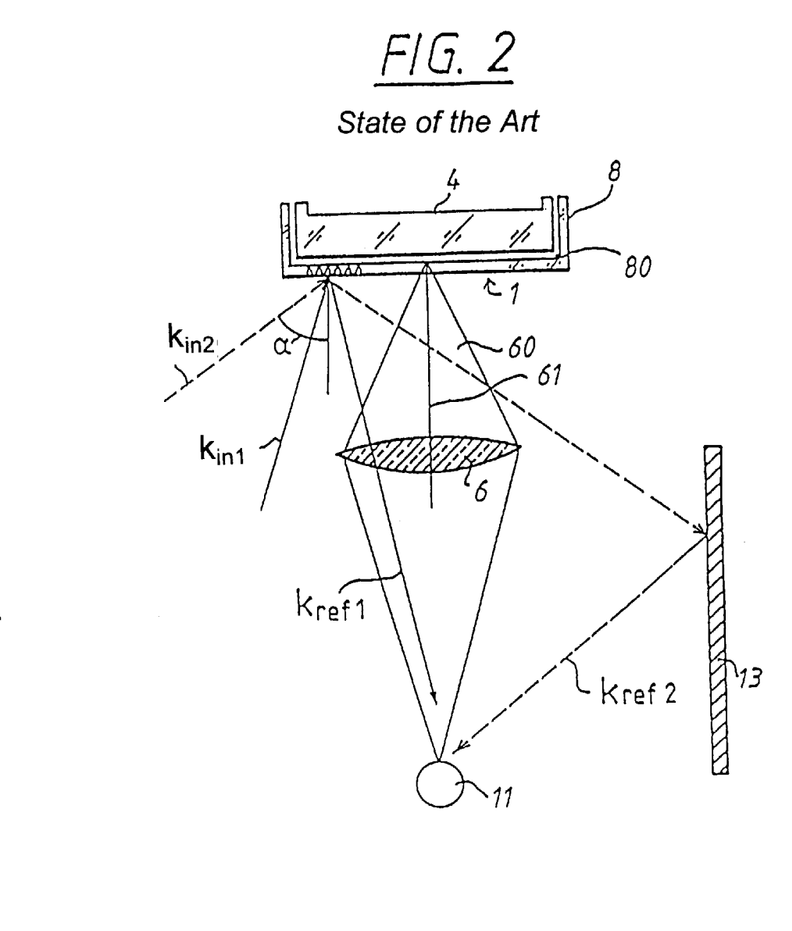
FIG. 2 is a diagrammatic representation of a luminescence waveguide sensor with detection of the volume luminescence according to the state of the art with a or coplanar beam path, in section, in the x-z plane.

FIG. 2 shows a beam path for such a case, the excitation radiation A is fed in direction $k_{ein}$ in the coupling-in plane x-z. Supplementary to FIG. 1, a liquid cell (8) with a sample (80) above the plane (1) of the sensor and a detector (11) are also shown, as are an aperture of the focusing lens system (6) with a detection beam path (60) and the optical axis (61) thereof. Forward coupling is shown for the coupling in. The magnitude of the coupling-in angle (α) between ($k_{ein}$) and sensor normal is to be so selected that the portion reflected off the sensor cannot pass directly through the aperture of the focusing lens system (6) onto the detector (11). For the purpose of illustration, two cases are shown in FIG. 2: one with a coupling-in angle (α) that is too small ($k_{ein1}$, $k_{ref1}$, continuous line) and one that is sufficiently large ($k_{ein2}$, $k_{ref2}$, broken line). Since the minimum coupling-in angle (a) required is determined by a aperture of the focusing lens system (6), a large-aperture focussing lens system of great light-transmitting capacity requires coupling-in angles far away from the perpendicular to the plane of the sensor.

The large coupling-in angle gives rise to the structural arrangement of the optical module for the operation of the waveguide sensor being significantly more complex than a version with angles close to the sensor normal.

Furthermore, even with an adequately large coupling-in angle (α) the reflected excitation radiation ($k_{ref}$) may strike the detector (11) merely as a result of a simple reflection off a wall (13). Even if known provisions are made to suppress scattered light, such as the dulling and blackening of the surfaces (13), there is hence the risk of interfering light being generated, which affects the detector (11). According to the state of the art, cut-off filters or band-pass filters are used to separate luminescence light and excitation light in luminescence detection. With filters of a given blockage ratio, the level of interfering radiation at the excitation wavelength limits the resolution of the measuring process.

Figure 3:
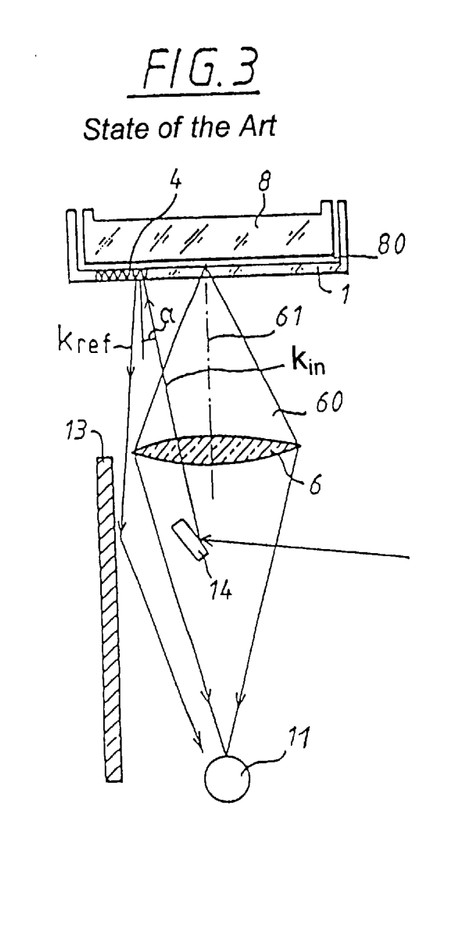
FIG. 3 is a diagrammatic representation of a modification of FIG. 2 with backward coupling.

As an alternative to FIG. 2, FIG. 3 shows a beam path in which some of the abovementioned problems are avoided by the use of backward coupling to excite the guided wave. In this case too, coupling-in angles α>30° should be avoided; coupling-in through the focussing lens system (6) is shown as an example in FIG. 3. This configuration is disadvantageous especially for high-sensitivity luminescence detection: interfering light may occur close to the detector (11) also as a result of scattering at the surfaces of the optical components used, especially a mirror (14) and the focusing lens system (6).

In addition, interfering light can again be conveyed to the detector (11) by a simple reflection off the wall (13).

Figure 4A:
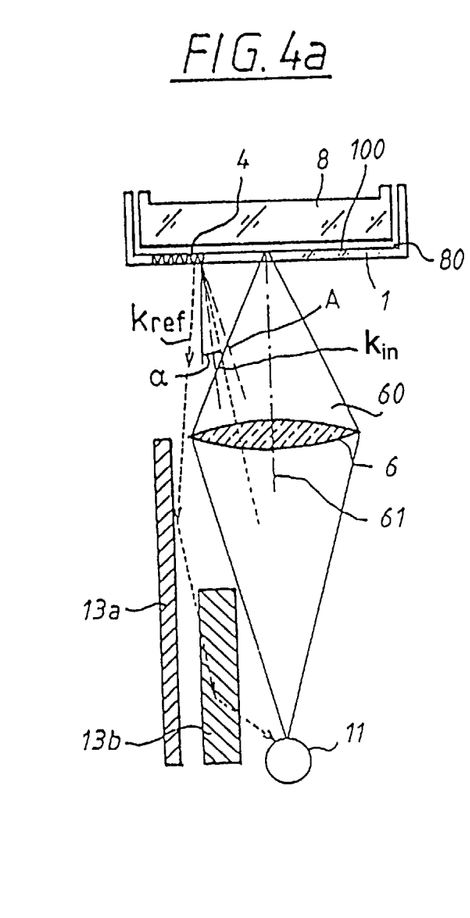
FIG. 4a is a section in an x-z plane of an arrangement according to FIG. 1.
Figure 4B:
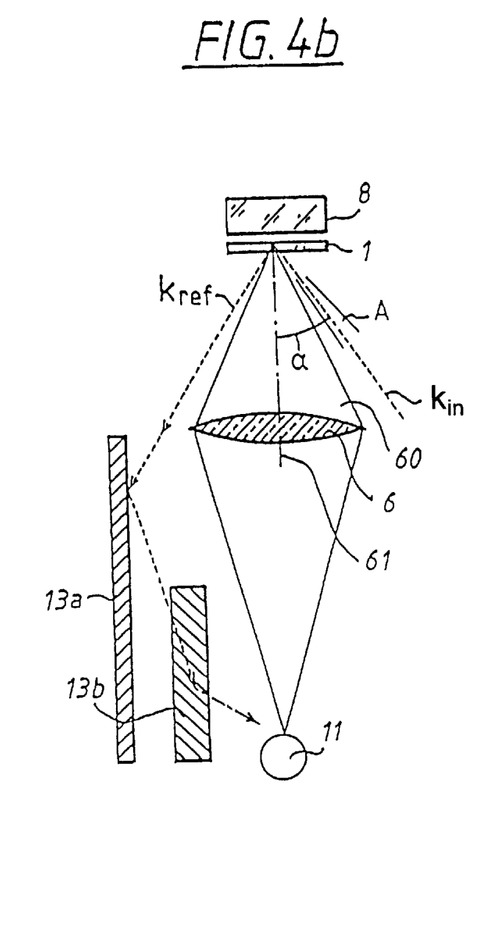

FIG. 4a shows in x-z section, and FIG. 4b in y-z section, how the configuration according to FIG. 1, in which the entry plane (2) is tilted relative to the coupling-in plane, affects the interfering signals. An important point is that the sections x-z and y-z each show the projection of the k-vectors onto the plane of section, this being indicated by the broken-line representation of the vectors. Backward coupling is selected for the coupling-in; because the plane of incidence (2) is tilted relative to the illustrated x-z coupling-in plane (3) the excitation light can be conveyed past the lens (6). Compared with the configurations in FIGS. 2 and 3, it is important that, with the same lens (6) aperture, the angles in the x-z and y-z planes necessary for passing the lens (6) at the side are smaller, for example where a =Θ, tan(x is smaller by the factor √2 compared with the case of "all k-vectors in the x-z plane".

However the effect of the tilted coupling-in plane (3) on the behavior of the reflected portions of radiation is decisive, as a result of the tilting at least two reflections are necessary to bring radiation from the excitation light beam (A), with the optical axis on the wave vector ($k_{ein}$) shown, into the detection beam path (60) and into the region of the detector (11) there. In contrast, in the coplanar configuration according to FIGS. 2 or 3, just a single reflection off a wall can have that effect.

There are therefore shown in FIGS. 4a and 4b two portions of walls (13a) and (13b), in each drawing the wall shown in section is indicated by a continuous line, and the wall lying in the plane of the drawing is shown by a broken line. As a result of the increase in the number of reflections required to introduce interfering radiation into the detector (11), the efficiency of all provisions for the suppression of interference radiation, such as the dulling or blackening of surfaces or the use of light traps, is significantly improved.

The effect of reflections off the walls (13) of the optical system or off the sensor (1) and the liquid cell (8) could theoretically also be avoided by the use of oblique angles unequal to 90° in the formation and positioning of the components. However the suppression of interfering signals would accordingly depend on the detailed geometry for excitation and coupling out. Even small changes in the sensor design would entail making changes to all parts of the hardware. For a design of the fluid cell (8) and reading system that is as universal as possible, the use of tilted optical planes (2), (3) is clearly preferably to the arrangement having oblique structural elements and boundary surfaces.

The reliable physical discrimination between luminescence signal and direct beam portions facilitates background-noise-free luminescence detection and hence creates conditions in which even high-sensitivity detection techniques, such as single photon counting, can be used in the detection system.

Figure 5:
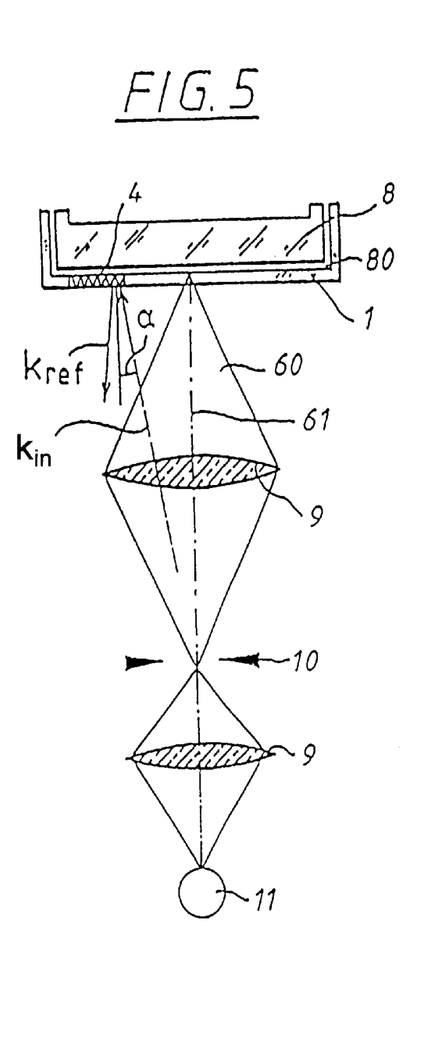
FIG. 5 shows in section an arrangement corresponding to FIG. 1 with a screen in a coupling-in plane.

A further provision for the suppression of external light caused by interfering portions of the excitation radiation is shown in FIG. 5. This shows a section through the coupling-in plane (3) of FIG. 1 (corresponding to FIG. 4a). It is possible by the selection of the angle θ between entry plane (2) and coupling-in plane (3) to ensure that the excitation radiation with ($k_{ein}$) does not pass through the focusing lens system (9) for the luminescence radiation but, physically separated outside the illustrated plane, passes by (9) onto the coupling-in grating (4). The luminescence radiation excited in the region of the guided wave (5) is projected by the focusing lens system (9) first of all into an intermediate image plane in which a screen (10) blanks out light from undesired areas of the sensor surface. As a result scattered light from the region of the coupling-in grating (4) caused, for example, by increased surface roughness of the wave-guiding layer (1) in the structured area or by inherent luminescence of the substrate (not shown in FIG. 5) below the wave-guiding layer (1), can be blanked out prior to the detector (11). The optical axis (61) of the detection beam path (60) and its entire geometry is hence kept clean.

Figure 7:
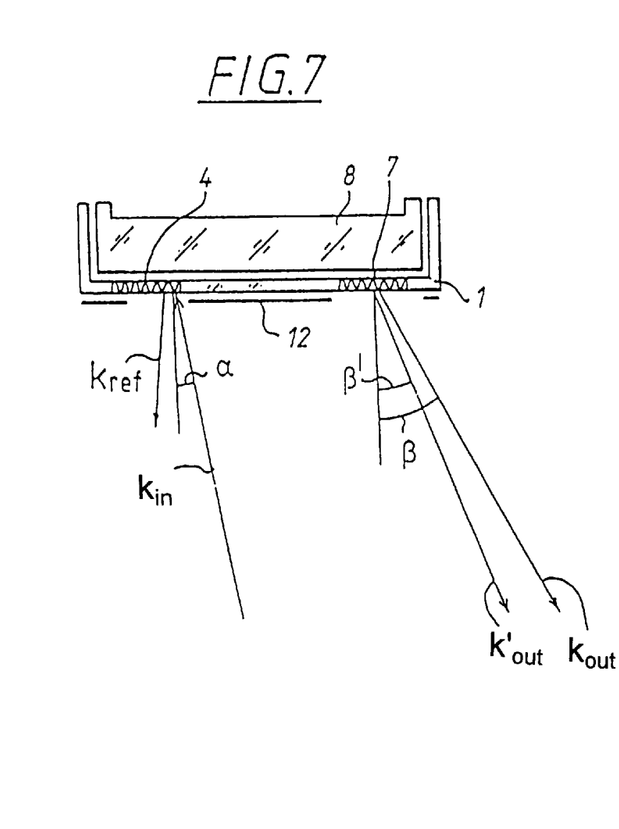
FIG. 7 shows an arrangement corresponding to FIG. 6 in section in the coupling-in plane.

The configuration for luminescence detection using waveguide detection is shown in FIG. 6. The coupling-in of the excitation radiation (A) with its axis of symmetry and wave vector ($k_{ein}$) and the propagation of the guided wave (5) is analogous to the volume detection shown in FIG. 1. The difference is that, in the case of waveguide detection, the luminescence radiation coupled back into the wave-guiding layer (1) is coupled out by a coupling-out grating (7), which is physically separate from the coupling-in grating (4). The coupling-out grating (7) may have a different grating constant from the coupling-in grating (4). The coupling-out angles for the coupled-in radiation ($k_{aus}$) transmitted through the waveguide and for the luminescence radiation ($k'_{aus}$) coupled into the waveguide are indicated by β and β'. The angles β and β' are different on account of the Stokes shift between excitation and luminescence radiation and the dispersion of the coupling-out grating (7). The two are consequently geometrically separated. For luminescence detection by means of waveguide detection, the arrangement in FIG. (7) is again shown as a cross-section in the coupling-in plane (3). In addition to the provisions for background-noise-free detection already mentioned, a further provision illustrated here is the use of a screen (12) close to the underside of the sensor. This reduces interfering radiation, which may occur in the region of the guided excitation wave (5) between coupling-in grating (4) and coupling-out grating (7), for example as a result of the inherent luminescence of the substrate material (not shown in FIG. 7) lying beneath the wave-guiding layer (1) or as a result of the luminescence of molecules in the liquid volume above the region of the sample (8) excited by the guided wave (5).

Figure 8:
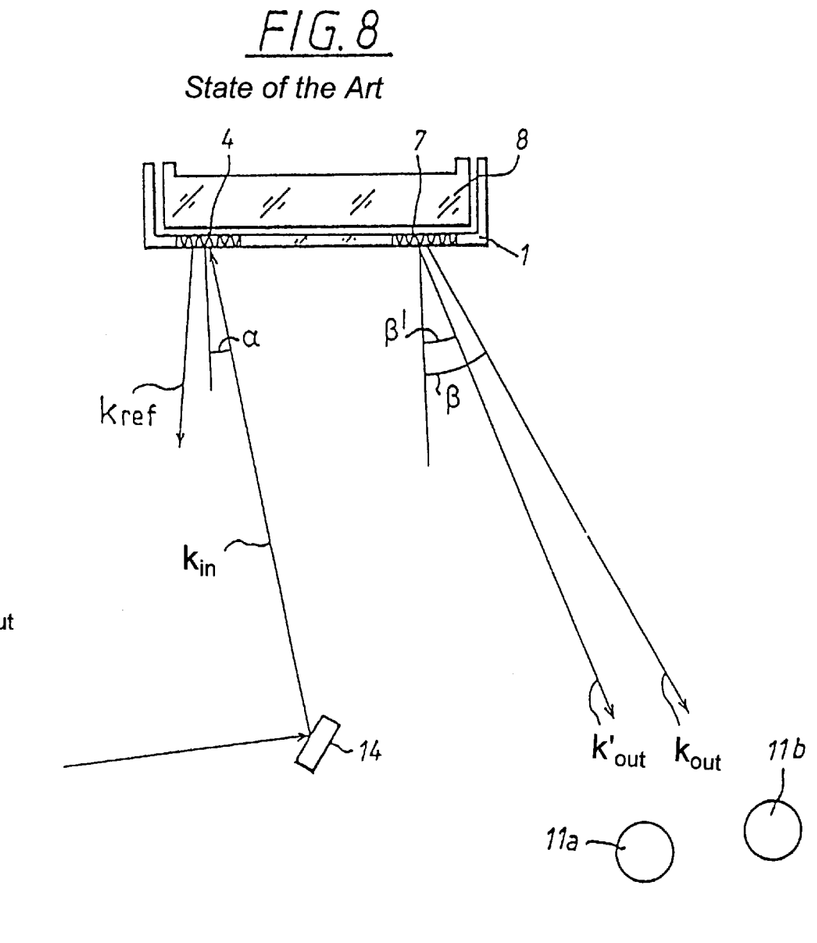
FIG. 8 is a section in the x-z plane of a known arrangement with waveguide detection in which a plane of incidence, a coupling-in plane and a direction of detection are coplanar (corresponding to FIG. 1 of WO 95/33198)
Figure 9A:
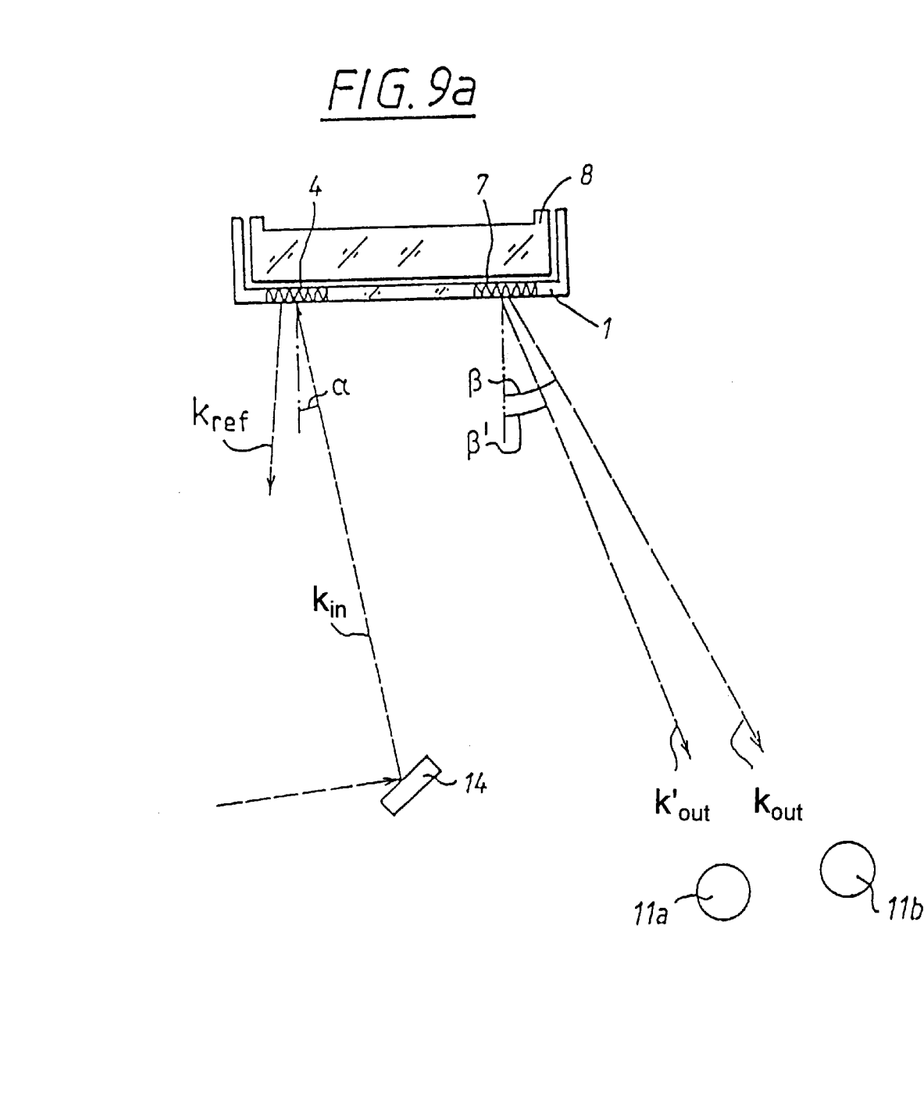
FIG. 9a is a section in the x-z plane of an arrangement according to FIG. 6.
Figure 9B:
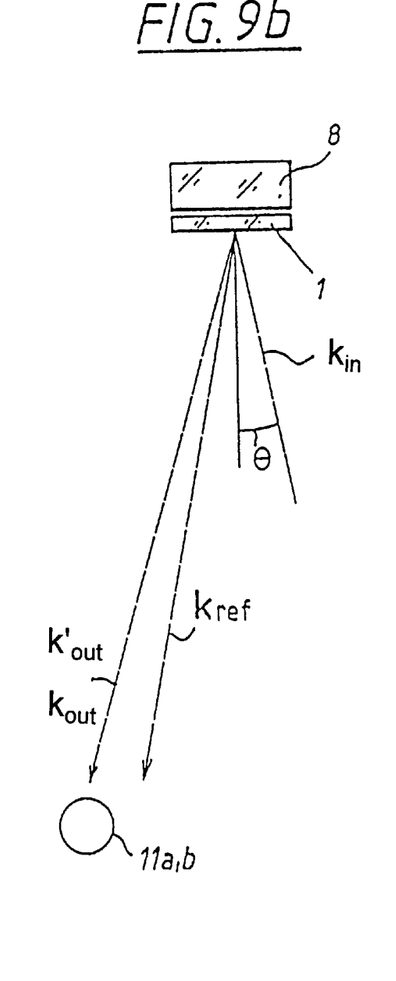

In the case of luminescence detection by way of the waveguide, the advantages of different coupling-in (3) and entry planes (2) are shown by way of FIG. 8 (state of the art) in comparison with the example according to the invention of FIGS. 9a and 9b. FIG. 8 is a section in the coupling-in plane (x-z plane) for coupling in by means of backward coupling. The incident light beam ($k_{ein}$) is fed to the waveguide (1) by a mirror (14). It should be noted that the geometric dimensions of the mirror (14) present an obstacle to miniaturization of the and the optical arrangement since the mirror (14) and the detectors (11a) and (11b) must, on account of their size, have a minimum distance between them that is far greater than the length of the waveguide (1). Omission of the mirror (14) would necessitate passing the excitation radiation far below the detectors (11a) and (11b), which would also, again, hinder miniaturization and compact design of the optical arrangement.

For the waveguide detection method, the reflected excitation radiation can, unlike in the case of detection of the volume luminescence, pass into the region of the detector (11) by means of a simple reflection off the ordinary structural elements of the sensor. As in the case of volume luminescence detection, however, when the plane of incidence (2) is tilted relative to the coupling-in plane (3) at least one more reflection is required in order to bring the reflected excitation radiation to the detector (11) than when that plane is not tilted.

The case according to the invention of tilted plane of incidence (2) and coupling-in plane (3) for waveguide luminescence detection is illustrated in FIGS. 9a and 9b, for the wave vectors $k_{ein}$, $k_{ref}$, $k_{aus}$, $k'_{aus}$ the projections into the plane of section x-z in FIG. 9a and y-z in FIG. 9b (indicated by the broken lines for the vectors) are shown. The mirror (14) or another deflection system for the excitation radiation $k_{ein}$ may be positioned outside the coupling-in plane (3) so that, as a result of the tilting of the beams, shadows cast by optical elements can be avoided. FIG. 9b in addition shows with the y-z section that, as a result of the tilting, all beam portions (excitation ($k_{ein}$), reflected excitation ($k_{ref}$), coupling out excitation light ($k_{aus}$), coupling out luminescence light ($k'_{aus}$)) are physically separate. The angles for incident excitation radiation (α) and excitation radiation coupled-out again (β) are always different when the grating periods of excitation grating (4) and coupling-out grating (7) are different. This is true of all cases that are relevant for practical purposes as a result of the different coupling geometry (excitation by way of backward coupling, coupling out by way of forward coupling).

Common to all described geometries with tilted coupling-in plane (3) and entry plane (2) is that, as a result of the tilting of those two planes (2), (3), there is a physical separation of the light signals involved, which significantly reduces the requirement for other provisions for discrimination between those beam portions, thus making possible the desired miniaturization both of the waveguide sensor and the entire optical arrangement.

All optical elements for the operation of the sensor can be arranged below the plane of the sensor, which is advantageous for the operation of such sensors in automated analysis systems; sensors and samples and also liquid media can be supplied from above, and measurement can be effected from below.

In addition, all optical elements for operation of the sensor can be produced in a compact module having small external dimensions. The light source being used may be a laser diode, a light-emitting diode or a super light-emitting diode, with optical and mechanical elements for the beam formation and the adjustment of the coupling-in angles, for example by rotation or displacement of optical elements -, and a beam guidance and shaping system for the outgoing and coupled-out radiation and an associated detection system. The latter may also be supplemented by a reference channel as a measure of the intensity of the coupled-in radiation.

If, owing to the excitation wavelength chosen, the laser light source to be used has dimensions that are significantly greater than those of the integrated module, the laser radiation is fed to the integrated module by means of an optical waveguide, preferably in an arrangement that preserves polarization.

The embodiments of the invention described in the Examples are preferred.

EXAMPLE EMBODIMENT 1

Fluorescence coupled into and guided in the waveguide

The light of a green HeNe laser (wavelength 543 nm; Melles Griot) is coupled into a waveguide (wave-guiding layer: 150 nm $TiO_2$, substrate: glass) via a rutile prism (Halle) and, by way of the evanescent field, excites a dye solution (rhodamine 6G, $10^{-6}$M) which is present in drop form on the waveguide. A detection system, consisting of a 50 mm focussing lens (Spindler & Hoyer), two 550 nm cut-off filters (Schott) and an Si-PIN photodiode (UDT) arranged at a distance of 5 cm below the transducer, detects the fluorescence light. On the one hand the signal radiated into the solid angle is detected, and on the other hand the fluorescence light coupled into the waveguide and coupled out at a coupling grating (period: 400 nm) is detected. The signal coupled out at the coupling grating, which is radiated at an angle different from the excitation light according to the dispersion properties of the coupling grating, is 50% stronger than the portion radiated into the solid angle as measured by the same detector.

EXAMPLE EMBODIMENT 2

Increase in the signal-to-noise ratio as a result of the use of crossed polarizers; fluorescence coupled into and guided in the waveguide in TE-polarisation The light of a linearly polarized HeNe laser (wavelength 633 nm; 1 mW; Melles Griot) is coupled by way of a coupling grating into a waveguide (wave-guiding layer: 150 nm $Ta_2O_5$, substrate: Corning glass C7059) and, by way of the evanescent field, excites an approximately 50 nm thick polymer matrix which has been applied by spin-coating and in which a dye is homogeneously distributed (Ciba dye WA 3010, $10^{-9}$M). TE- or TM-polarized excitation light, as desired, can be coupled in by means of a retarding plate (Lambda/2 for 633 nm; Rocky Mountains Instr.) and polarizer (Spindler & Hoyer). A detection system consisting of analyzer, notch filter (Kaiser) and a CCD camera (Kappa) arranged 10 cm below the transducer detects the fluorescence light coupled into the waveguide and coupled out at the coupling grating (period: 320 nm). For both excitation polarizations, the signal intensities are measured both with a crossed analyzer and with a parallel analyzer. If TE-polarized light is coupled in, the ratio of the two fluorescence components TE/TM coupled out at the coupling grating is 7:1.

If TM-polarized light is coupled in, the ratio of the two fluorescence components TE/TM coupled out at the coupling grating is 2.5:1.

What is claimed is:

1. An integrated-optical luminescence sensor for a sample, said integrated-optical luminescence sensor comprising:
   a light source operable to output an excitation light beam having a first optical axes;
   a planar waveguide operable to receive the excitation light beam and to form a guided wave from the excitation light beam and further operable to create an evanescent field which interacts with the sample to create luminescence light;
   a detector operable to detect at least a portion of the luminescence light; and
   at least one of (a) a detection beam path along which travels at least a portion of the luminescence light, said detection beam path having a second optical axis projecting from said planar waveguide, and (b) a coupling-out grating operable to couple out at least a portion of the luminescence light in said waveguide,
   wherein the luminescence light is physically separated from the excitation light beam by at least one of the following:
   a skew geometric arrangement of the first and second optical axis;
   at least one polarization-selective component being located in the detection beam path;
   at least one polarization-selective component being located in a path of the luminescence light coupled out from said coupled-out grating; and
   at least one polarization-selective component being located in the portion of the luminescence light coupled out from said coupled-out grating, wherein a coupled-in grating operable to couple in the excitation light beam into said planar waveguide is further operable to act as said couple-out grating.

2. An integrated-optical luminescence sensor as claimed in claim 1, further comprising a coupling-in grating operable to couple in the excitation light beam into said planar waveguide.

3. An integrated-optical luminescence sensor as claimed in claim 1, wherein said planar waveguide and said light source are arranged such that an angle than 1° is formed between a coupling-in plane, which is defined by a normal to said planar waveguide and a wave vector of the guided wave, and an entry plane, which is defined by the wave vector of the guided wave and a wave vector of the excitation light beam.

4. An integrated-optical luminescence sensor as claimed in claim 1, wherein said planar waveguide and said light source are arranged such that said angle is greater than an angle of divergence of the excitation light beam.

5. An integrated-optical luminescence sensor as claimed in claim 1, further comprising a focusing lens system within the detection beam path and being operable to capture at least a portion of the luminescence light and feed it to said detector.

6. An integrated-optical sensor as claimed in claim 1, further comprising a coupling-in grating arranged on said planar waveguide and operable to couple in the excitation light beam into said planar waveguide and a coupling-out grating operable to couple out at least a portion of the luminescence light from said waveguide, wherein the portion of the luminescence light is fed to said detector.

7. An integrated-optical luminescence sensor as claimed in claim 3, wherein said planar waveguide and said light source are arranged such that said angle is less than 30°.

8. An integrated-optical luminescence sensor as claimed in claim 3, wherein said planar waveguide and said light source are arranged such that said angle is less than 15°.

9. An integrated-optical luminescence sensor as claimed in claim 1, wherein said light source is operable to output a substantially transversely magnetically polarized excitation light beam for excitation of a transversely magnetically polarized excitation light mode in said planar waveguide or a substantially transversely electrically polarized excitation light beam for excitation of transversely electrically polarized light mode in said planar waveguide.

10. An integrated-optical luminescence sensor as claimed in claim 1, wherein said light source is operable to output a substantially transversely magnetically polarized excitation light beam for excitation of a transversely magnetically polarized excitation light mode in said planar waveguide or a substantially transversely electrically polarized excitation light beam for excitation of transversely electrically polarized light mode in said planar waveguide and wherein the excitation light mode in said planar waveguide is different from a polarization of the portion of the luminescence light to be detected by said detector.

11. An integrated-optical luminescence sensor as claimed in claim 10, wherein said detector is operable to detect a transversely magnetically polarized portion of the luminescence light when a totally electrically polarized excitation light mode has been excited in said planar waveguide.

12. An integrated-optical luminescence sensor as claimed in claim 10, wherein said detector is operable to detect a transversely magnetically polarized portion of the luminescence light when a totally magnetically polarized excitation light mode has been excited in said planar waveguide.

13. An integrated-optical luminescence sensor as claimed in claim 1, further comprising a plurality of planar waveguides similar to said planar waveguide, wherein said plurality of planar waveguides have either one common coupling-in grating or each of said plurality of planar waveguides has a coupling-in grating.

14. An integrated-optical luminescence sensor as claimed in claim 1, further comprising a plurality of planar waveguides similar to said planar waveguide, wherein said plurality of planar waveguides have either one common coupling-out grating or each of said plurality of planar waveguides has a coupling-out grating.

15. An integrated-optical luminescence sensor as claimed in claim 1, further comprising a plurality of planar waveguides similar to said planar waveguide, wherein said plurality of planar waveguides have either one common coupling-in grating or each of said plurality of planar waveguides has a coupling-in grating and either one common coupling-out grating or each of said plurality of planar waveguides has a coupling-out grating.

16. An integrated-optical luminescence sensor as claimed in claim 9, further comprising an additional polarization-selective component located in the excitation beam path, said additional polarization-selective component being operable to select whether a substantially transversely magnetically polarized excitation light beam is inputted into said planar waveguide or a substantially transversely electrically polarized excitation light beam is inputted into said planar waveguide.

17. An integrated-optical luminescence sensor as claimed in claim 10, further comprising an additional polarization-selective component located in the excitation beam path, said additional polarization-selective component being operable to select whether a substantially transversely magnetically polarized excitation light beam is inputted into said planar waveguide or a substantially transversely electrically polarized excitation light beam is inputted into said planar waveguide.

* * * * *